United States Patent [19]

Ono

[11] 4,008,311
[45] Feb. 15, 1977

[54] COMPOSITION FOR CONTROLLING SEXUAL BEHAVIOR OF MAMMALS

[75] Inventor: Hiroomi Ono, Tokyo, Japan

[73] Assignee: Takeda Chemical Industries, Ltd., Osaka, Japan

[22] Filed: Mar. 14, 1975

[21] Appl. No.: 558,359

[30] Foreign Application Priority Data

Mar. 16, 1974 Japan .............................. 49-30245

[52] U.S. Cl. .............................. 424/240; 424/312
[51] Int. Cl.² ........................................ A61K 31/56
[58] Field of Search ................... 424/238, 240, 346

[56] References Cited

FOREIGN PATENTS OR APPLICATIONS 40,272  6/1972  Japan

OTHER PUBLICATIONS

Chemical Abstracts, vol. 78, (1973), p. 80004c.
Merck Index, 7th Ed., (1960), pp. 1018–1019.

*Primary Examiner*—V. D. Turner
*Attorney, Agent, or Firm*—Cushman, Darby & Cushman

[57] ABSTRACT

An injectable composition for controlling the sexual behavior of mammals containing as effective ingredients hexestrol difatty acid ester and testosterone fatty acid ester in a weight ratio of 0.5 to 10 : 10 to 0.5.

2 Claims, No Drawings

COMPOSITION FOR CONTROLLING SEXUAL BEHAVIOR OF MAMMALS

The present invention relates to a composition for controlling the sexual behavior of mammals containing as effective ingredients hexesterol difatty acid ester and testosterone fatty acid ester.

After maturation of pet animals and domesticated animals, there often occurs noise nuisance due to the clamor or barking of the male animals and the female animals in their mating season. Bites by dogs in their mating season have frequently occurred and have constituted a serious public nuisance. Moreover, bad management of reproduction in pet animals such as dogs and cats causes the appearance of stray pet animals such as stray dogs and cats.

Heretofore it has been known that continuous oral or parenteral administration of estrogenic or progesteronic substances to animals produces inhibition of spermatogenic function in male animals and infertility or artificial abortion in female animals.

Japanese Patent Publication No. 40270/1972 has disclosed that, when hexestrol dicaprylate (referred to as HESC hereinafter) is administered alone to animals in the dosage of 0.5 mg/kg of more, reproduction activity is suppressed in both male animals and female animals over several months and that reproduction capacity returns to the normal state thereafter. However, depending on the individual animals, it is sometimes accompanied by side effects such as momentary dejection, anorexia, loss in lustre of the hair, partial or whole depilation, edema of the prepuce, pollakisuria or dysuria due to disorders of the prostate glands, swelling of the breast (male), edema of the external genitalia owing to the continuation of the pseudoestrus and the like.

An object of this invention is to provide an injectable composition for controlling the sexual behavior of mammals, without giving any side effects.

Another object of this invention consists in suppressing the reproduction capacity of mammals for several months by a single injection, and thereafter the returning of the reproduction capacity to the normal state.

Other objects of this invention will be appear, hereafter.

In accordance with the present invention, there is provided an injectable composition for controlling the sexual behavior of mammals containing as effective ingredients hexestrol difatty acid ester (referred to as HESE hereinafter) and testosterone fatty acid ester (referred to as TE hereinafter).

Examples of the HESE to be used in accordance with the present invention include preferably diesters of hexestrol with fatty acid having 4 to 10 carbon atoms. The fatty acids which can be used for this purpose include straight, branched, saturated and unsaturated fatty acid. Particularly, butyric acid, valeric acid, caproic acid, enanthic acid, caprylic acid, pelargonic acid, capric acid and the like are preferably used. HESE can easily be obtained by reacting hexestrol with an anhydride, or acid halide, particularly acid chloride, of a fatty acid. Preferable examples of TE are esters of testosterone with fatty acid having 2 to 9 carbon atoms. The fatty acids which can be used for this purpose include straight, branched, saturated and unsaturated fatty acid. Particularly, acetic acid, propionic acid, butyric acid, valeric acid, caproic acid, enanthic acid, caprylic acid, β-cyclopentylpropionic acid and the like. The weight ratio of HESE to TE is selected from the range of 0.5 – 10 : 10 – 0.5 and generally the weight ratio is preferably from about 1 : 1 to about 1 : 3 and, in particular, the weight ratio of about 1 : 1 is most desirable. If TE is formulated in a large amount, the effect of HESE is a little reduced on account of the mutual antagonistic action. However, when recovery of the propagation ability is desired in a rather short period of time, favorable result will be obtained if TE is formulated in an amount of 5 to 10 times by weight as much as that of HESE.

In an injectable composition of the present invention a mixture of HESE and TE as effective ingredients may be formulated in any pharmaceutically acceptable liquid carrier. As to the liquid carrier, vegetable oils, for example, sesame oil, cotton-seed oil, peanut oil, rapeseed oil, olive oil and the like can be used. The effective ingredients may be suspended in an aqueous medium, with the aid of suitable suspending agents, for example, higher alcohol ether of polyoxyethylene (hereinafter referred to as POE), POE alkylaryl ether, POE fatty acid ester, POE sorbitan monofatty acid ester and POE hydrogenated castor oil and a suspension stabilizer, for example, carboxymethylcellulose, polyvinylpyrrolidone. In this case, said aqueous suspension can be prepared according to the known process per se, for example, by stirring fine particles of HESE and TE together with a dispersing agent in an amount of 1 to 20% by weight based upon said fine particles in water, and, if necessary, sodium carboxymethyl cellulose, polyvinyl pyrrolidone and the like can be used as suspension stabilizer in an amount of 0.2 to 10% by weight based upon the water used. The site of injection of the composition of the present invention is not particularly limited, but in general it is preferably injected intramuscularly or subcutaneously in the back, hip and the bottom of the ear portions of the subject mammals. The injectable composition of the present invention is preferably prepared at the concentration of 2 to 40 mg/ml of the effective ingredients. The dosage is selected suitably depending on the subject animals, sex, age, body weight and the like, or intended objects. For the purpose of controlling reproduction, a single administration of 0.2 to 5.5 mg/kg preferably 0.5 to 3.0 mg/kg, of the effective ingredients, causes loss of sexual desire and sexual activity in males and causes infertility in females for 4 to 5 months after injection. This can serve to prevent the birth of stray dogs and cats due to uncontrolled reproduction and disturbance of peoples sleep due to noise during the estrus period in the case of dogs and cats, and conception during grazing in the case of beef cattle. For the purpose of artificial abortion, if avoidance of conception is to be effected immediately after copulation, the composition of the present invention may be given in the same dosage as mentioned above in a single administration, if in the middle stage of pregnancy, the composition should be given in the same dosage two times at 2 to 3 day intervals and if in the terminal stage of pregnancy, the same dosage must be given 2 to 3 times within 3 to 7 days. In general, as for the effective dosage for these purposes, the combined dosage of HESE and TE for cats is one-half of the dosage for dogs and the combined dosage of HESE and TE for the males is 3 to 5 times as much as the dosage for the females and, furthermore, the combined dosage of HESE and TE for infant animals is about one-half of the combined dosage of HESE and TE for the adult animals.

The characteristics of the present composition for controlling the sexual behavior of mammals containing as effective ingredients HESE and TE are as follows:

1. The safety range of the effective dosage of HESE among the effective ingredients is wide and there occurs no side effect, for example, shock, depilation and the like in the animals given HESE and it can provide a reproduction inhibiting effect for several months with a single injection.

2. During the period in which the reproduction is effectively inhibited, the instinct inherent of the animals, for example, alertness is not lost in the case of a dog and they remain obedient and are kept easily during such period and, in addition, the animals are completely returned to the normal state after a certain period of time and the animals regain their reproduction ability.

3. In the case of male animals, when observed clinically by a specialist (Veterinary), abrupt abeyance of the secretion of semen as observed in the administration of HESE alone, does not occur, but a procedure of gradual decrease, abeyance, gradual increase and the recovery step of the secretion of the semen appears smoothly. The animals are quiescent at the time of semen collection and the properties of the collected semen can be observed easily and hence effectiveness and recovery of the reproduction activity can readily be determined.

4. Sedative effect on the animals in the estrus period appears rapidly and howling and irritation disappears on the next day after injection.

5. A combination of HESE and TE according to the present invention can inhibit the reproduction with a single administration thereof and hence it is a labor-saving and economic drug and it does not bear a heavy burden on the keeper.

It is to be understood that the following examples are solely for the purpose of illustration and not to be construed as limitation of this invention, and that many variations may be resorted to without departing from the spirit and scope of this invention.

EXAMPLE 1

0.4 Milliliter of injectable composition containing 10 mg of hexestrol dicaprylate dissolved in 1 ml of sesame oil was injected once in the dosage of 0.5 mg/kg into the back portion of a cross-bred Shiba-ken and spitz dog (8 kg in body weight, male, 4 years old) and the dog was observed for 2 months after injection. The semen was collected by the manual method.

Results of the Observation

Before injection, the dog showed anorexia, howled, and it was in an unstable mental condition and snarled at the keeper. The dog showed appetite from the next day after the injection and drank much water and it often had diarrhea. Atrophy of the testis became striking and the dog became obedient in character. It was observed to become slightly lean. Loss of hair inceased from about the 10th day on and dysuria was noted on around 14th day after injection and it continued for about 3 days.

Properties of the semen:

| | Volume of semen collected | State of the sperms |
| --- | --- | --- |
| Before injection | About 2 ml | +++ |
| 7th day | About 1.2 ml | ± |
| 14th day | About 0.5 ml | − |
| After 2 months | About 1 ml | ± |

Note:
+++ The sperms are very large in number and very active movements of sperms are observed.
++ The sperms are slightly decreased in number and active movements of sperms are observed.
+ The sperms are fairly decreased in number and slow movements are observed.
± The sperms are small in number and indefinite movements are observed.
− The sperms are very small in number and no movement is observed.

The dog was mated with a female dog 6 months after administration of HESC alone and the conception thereof was ascertained. After having confirmed that the reproduction capacity of the male dog returned to the normal state as before the injection. 0.4 Milliliter of injectable composition containing 20 mg of a mixture of an equal amount of hexestrol dibutyrate and testosterone enanthoate (referred to as TEN hereinafter) dissolved in 1 ml of sesame oil was injected intramuscularly in the dosage of 0.5 mg/kg of individual component, totaling 1.0 mg/kg, into the hip portion of the male dog. Before the injection, the volume of the semem collected was 2 ml, and the volume was decreased to 1.5 ml gradually from the 7th day after injection, and collection of the semen became impossible on the 40th day. Further, collection of a small amount (0.5 ml) of the semen became again possible by the manual method on the 60th day after the injection. The volume of semen collected returned to the normal state (2 ml) after an additional 30 days. Neither depilation nor dysuria was observed during that period.

EXAMPLE 2

0.3 Milliliter of an injectable composition containing 10 mg of hexestrol dicaprylate in 1 ml of sesame oil was injected subcutaneously in a single dosage of 0.5 mg/kg into the bottom of the ear-portion of a poodle dog (6 kg in body weight, male, 3 years old) and the dog was observed for 2 months. Collection of semen was attempted by the manual method during that period.

Results of the Observation

Before the injection, the dog snarled at people at about 8 p.m. and showed an irregular appetite. The dog howled and sometimes strayed. The dog showed dysuria and loss of appetite from the next day after the injection of the composition. The dog showed a state of shock and its ferocity was completely lost. The testis were atrophied to one-third after about one month. The loss of hair was not so striking, but lustre of the hair was lost.

Properties of the semen:

| | Volume of the semen collected | State of the sperms |
| --- | --- | --- |
| Before injection | About 1.5 ml | +++ |
| 7th day | About 0.5 ml | − |
| 14th day | Almost only the first fluid was collected. | ± |
| After 2 months | About 0.5 ml | ± |

The dog was mated with a female dog 6 months after the injection and conceived. After having confirmed that the reproduction ability of the dog had returned to the normal state, 0.3 ml of injectable composition containing 10 mg of hexestrol dicaprylate and 10 mg of testosterone enanthate in 1 ml of sesame oil was injected in the dosage of 0.5 mg/kg of each component. Before the injection, the volume of the semen collected was 1.5 ml and was reduced to about two-third 1.0 ml on the 7th day after the injection and about the same volume (1.0 ml) of the semen was collected 2 months after the injection. The number of sperms was reduced markedly as follows: before injection +++; 7th day after injection ±; 14th day after injection —; 2 months after injection —. There could be observed no side effects such as depilation, loss of the lustre of the hair, dysuria and the like during said period and the dog showed slightly improved appetite. The dog still had sexual desire and the mating for a short period of time was attempted a few times, resulting in unsuccessful conception.

EXAMPLE 3

0.45 Milliliter of injectable composition containing 5 mg of hexestrol dicaprylate in 1 ml of cotton seed oil was injected intramuscularly in the dosage of 0.5 mg/kg into the back portion of maltese dog (4.5 kg in body weight, male, 3 years old). After depression for a short period of time, lustre of the hair was lost and dysuria was noted. Virility was completely recovered in the 6th month after the injection. The dog became sensitive to the estruation of the female dog living with it. Then 0.45 ml of injectable composition containing 5 mg each of hexestrol dicaprylate and testosterone enanthate in 1 ml of cotton seed oil was injected subcutaneously in the dosage of 0.5 mg/kg of each compound into the back portion of the dog. When observed one month after the injection, there was found no side effect and volume and the state of the semen collected showed similar to those shown in Example 2.

EXAMPLE 4

Dachshund (5 kg in body weight, male, 4 years old) was sensitive to a female dog, howled and showed ferocity and after 0.5 ml of injectable composition contanting 5 mg of hexestrol dicaprylate and 25 mg of testosterone enanthate in 1 ml of sesame oil was injected intramuscularly in the dosage of 0.5 mg/kg and 2.5 mg/kg, respectively, into the hip portion of the dog concomittantly. The volume of the semen collected before the injection was 2.8 ml, whereas the volume of the semen collected respectively on the 7th, 14th and the 21st day after the injection were reduced to 1.5 ml and at the same time the sperms were reduced markedly in number. After the injection, the volume of the dog's bark was decreased and the dog became calm and there was observed no side effects as in another dog given the same dosage. The characteristic of the dog returned to the normal one after about 3 months. Consequently, when the weight ratio of HESC to TE is 1 : 5 or more, the action of HESE tends to be suppressed slightly and hence, if recovery of the reproduction activity is to be desired after a short period of about 3 months, it is desirable that TE is incorporated in an amount of 5 to 10 times as much.

EXAMPLE 5

For the purpose of prevention of straying and the noisy state in the autumn mating season, 0.5 ml of injectable composition containing 2 mg of hexestrol dicaprylate and 2 mg of testosterone enanthate in 1 ml of olive oil was injected intramuscularly in the dosage of 0.25 mg/kg of each component into the back portion of a black Japanese cat (4 kg in body weight, male, 2 years old). After the injection the cat did not leave home and there was found no clinical change and a year passed. It was impossible to collect the semen during that period, but atrophy of the testis was observed continuously from the 2nd week after injection and thereafter.

EXAMPLE 6

5 Milliliters of injectable composition containing 10 mg of hexestrol dicaprylate and 50 mg of testosterone enanthate in 1 ml of sesame oil was injected intramuscularly into the hip portions of 5 Japanese cows aged 1 year and 5 months to give 50 mg of HESC and 250 mg of TEN and they were allowed to graze together with 100 other cattles including bulls for 4 months and thereafter they were examined for conception. They were not pregnant. However, 3 other cows not-treated were all found to be pregnant, there was no side effects on the cows injected with the composition of the present invention.

EXAMPLE 7

The following preparations (1) – (5) of the present invention were injected into animals.

(1) 1.0 Milliliter of injectable composition containing 3.25 mg of hexestrol dibutyrate and 6.5 mg of testosterone β-cyclopentylpropionate in 1 ml of peanut oil was injected intramuscularly in the dosage of 0.5 mg/kg of hexesterol dibutyrate and 1 mg/kg of testosterone β-cyclopentylpropionate into the back portion of a dog (6.5 kg in body weight, male, 3 years old).

(2) 1.0 Milliliter of injectable composition containing 16 mg of hexestrol dibutyrate and 8.0 mg of testosterone enanthate in 1 ml of olive oil was injected intramuscularly in the dosage of 2 mg/kg of hexesterol dibutyrate and 1 mg/kg of testosterone enanthate into the back portion of a dog (8.0 kg in body weight, male, 4 years old).

(3) 1.0 Milliliter of injectable composition containing 3.5 mg of hexestrol dicaprylate and 3.5 mg of testosterone enanthate suspended in 1 ml of water with the aid of 20 mg of carboxymethylcellulose and 1 mg of polyoxyethylene sorbitan monooleate was injected intramuscularly in the dosage of 0.5 mg/kg of hexestrol dicaprylate and 0.5 mg/kg of testosterone enanthate into the back portion of a dog (7.0 kg in body weight, male, 4 years old).

(4) 0.5 Milliliter of injectable composition containing 0.6 mg of hexestrol dienanthate and 0.9 mg of testosterone enanthate in 0.5 ml of cottonseed oil was injected subcutaneously in the dosage of 0.2 mg/kg of hexestrol dienanthate and 0.3 mg/kg of testosterone enanthate into the back portion of a cat (3.0 kg in body weight, male, 2 years old).

(5) 0.5 Milliliter of injectable composition containing 1.0 mg of hexestrol dipelargonate and 1.0 mg of testosterone caprylate in 0.5 ml of sesame oil was injected subcutaneously in the dosage of 0.25 mg/kg of hexestrol dipelargonate and 0.25 mg/kg of testosterone caprylate into the back portion of a cat (4.0 kg in body weight, male, 3 years old).

What is claimed is:

1. A method for causing loss of sexual desire and sexual activity in a male dog comprising administering to said dog an injectable composition containing (1) hexesterol dicaprylate and (2) testosterone enanthate in a weight ratio of (1) to (2) of 1:1-3 as active ingredients and a pharmaceutically acceptable liquid carrier in a dosage of 0.5–3.0 mg/kg body weight of the active ingredients.

2. A method according to claim 1 wherein the weight ratio of (1) to (2) is about 1:1.

* * * * *